United States Patent
Saito et al.

[11] Patent Number: 5,968,801
[45] Date of Patent: Oct. 19, 1999

[54] POLYHYDROXYALKANOATE DEPOLYMERASE AND PROCESS FOR PRODUCING THE SAME

[75] Inventors: Yuji Saito; Masako Shibayama, both of Tokyo; Hidehi Takebe; Toshio Matsunobu, both of Kanagawa, all of Japan

[73] Assignees: Taisei Corporation; Meiji Seika Kasha, Ltd., both of Tokyo, Japan

[21] Appl. No.: 09/003,086

[22] Filed: Jan. 5, 1998

[30] Foreign Application Priority Data

Jan. 8, 1997 [JP] Japan ..................................... 9-001198

[51] Int. Cl.⁶ .............................. C12N 9/18; C12P 21/04; C12P 21/06
[52] U.S. Cl. ........................ 435/197; 435/71.1; 435/69.1
[58] Field of Search ..................... 530/326, 350; 435/69.1, 197, 71.1

*Primary Examiner*—Robert A. Wax
*Assistant Examiner*—Devesh Srivastava
*Attorney, Agent, or Firm*—Fish & Richardson P.C.

[57] ABSTRACT

The present invention relates to polyhydroxyalkanoate depolymerase having a N-terminal fragment of the amino acid sequence of SEQ ID NO: 1 and having a molecular weight of about 33,000 as determined by SDS polyacrylamide gel electrophoresis; a process for producing polyhydroxyalkanoate depolymerase, comprising culturing in a medium a microorganism which belongs to the genus Corynebacterium and has the ability to produce the polyhydroxyalkanoate depolymerase and recovering the polyhydroxyalkanoate depolymerase from the resulting culture; and a process for producing polyhydroxyalkanoate depolymerase, comprising culturing in a medium a transformant transformed with a recombinant vector containing a gene of the polyhydroxyalkanoate depolymerase and recovering the polyhydroxyalkanoate depolymerase from the resulting culture. According to the present invention, there can be provided novel PHA depolymerase with the activity of decomposing ω-hydroxyalkanoates, particularly 4HB homopolyester or copolymerized polyesters containing said homopolyester, and a process of efficiently producing the enzyme.

3 Claims, 6 Drawing Sheets

# POLYHYDROXYALKANOATE DEPOLYMERASE AND PROCESS FOR PRODUCING THE SAME

FIELD OF THE INVENTION

The present invention relates to novel polyhydroxyalkanoate depolymerase and a process for producing the same.

BACKGROUND OF THE INVENTION

Polyhydroxyalkanoates (PHAS) accumulated intracellularly as an energy storage substance in microorganisms are biodegradable thermoplastic polyester and draw attention as a biodegradable plastic material. The most representative example of PHAs is [R]-3-hydroxybutyrate (3HB) homopolyester, that is, P([R]-3HB), which has similar strength to that of polypropylene and excellent biodegradability. However, these were not put to practical use as biodegradable plastic because of extremely brittle properties.

Meanwhile, biosynthesis of copolymerized polyesters such as [R]-3HB/4-hydroxybutyrate (4HB) copolymers depending on the microorganisms and carbon source used has been confirmed recently. These copolymerized polyesters exhibit a wide variety of physical properties ranging from crystalline plastic to highly elastic rubber depending on the type of constituent monomer unit and the composition of copolymer, so their use as biodegradable plastic is expected.

PHA depolymerases secreted extracellularly by microorganisms such as *Alcaligenes faecalis, Comamonas acidovorans, Pseudomonas picketii, Pseudomonas lemoignei, Pseudomonas testosteroni, Penicillium pinophilum* etc. have been confirmed as representative enzymes decomposing PHA. It is revealed that the active site of these enzymes is a serine residue and the enzyme activity is greatly influenced by the degree of crystallinity of polyester. Lipase produced by fungi such as *Rizopus delemer* etc. has also been confirmed as an enzyme decomposing PHA and is known to decompose side-chain-free PHAs such as polypropyllactone and polycaprolactone. As described, the enzymes decomposing PHA confirmed up to now are only PHA depolymerase and lipase.

SUMMARY OF THE INVENTION

The object of the present invention is to provide novel PHA depolymerase and a process for producing said enzyme efficiently.

As a result of their eager study on PHA depolymerase in active sludge, the present inventors found that the strain IM-1 belonging to the genus Corynebacterium produces novel PVA depolymerase extracellularly, and they arrived thereby at the present invention.

The present invention relates to PHA depolymerase having a N-terminal fragment of the amino acid sequence of SEQ ID NO: 1 and having a molecular weight of about 33,000 as determined by SDS polyacrylamide gel electrophoresis.

Further, the present relates to a process for producing the PHA depolymerase which comprises culturing in a medium a microorganism having the ability to produce the PHA depolymerase and recovering the PHA depolymerase from the resulting culture.

Furthermore, the present invention relates to a process for producing the PHA depolymerase which comprises culturing in a medium a transformant transformed with a recombinant vector containing a gene of the PHA depolymerase and recovering the PHA depolymerase from the resulting culture.

DETAILED DESCRIPTION OF THE INVENTION

Hereinafter, the present invention is described in detail.

The PHA depolymerase of the present invention has the following physicochemical properties:

1. Action and substrate specificity

It decomposes homopolyesters such as 3-hydroxypropionate, 4-hydroxybutyrate (4HB), 5-hydroxyvalerate, 6-hydroxycapronate etc. or copolymerized polyesters containing them. Among them, the activity of decomposing 4HB homopolyesters or 4HB-containing copolymerized polyesters is particularly high.

The activity of the present enzyme was examined in the following manner.

(1) Five 3HB–4HB random copolymers biosynthesized by *Alcaligenes eutrophus* or *Comamonas acidovorans* were used to examine the activity of the present enzyme. The number average molecular weight and 4HB of each copolymer are shown in Table 1.

TABLE 1

|  | average number molecular weight | 4HB content (mol-%) |
|---|---|---|
| Copolymer 1 | 712,500 | 0 |
| Copolymer 2 | 83,800 | 14 |
| Copolymer 3 | 177,900 | 41 |
| Copolymer 4 | 140,700 | 69 |
| Copolymer 5 | 86,300 | 97 |

Copolymers 1 to 5 were formed into films by solvent casting and the films were cut into small pieces 1 by 1 cm square (each weighing about 8 mg) which were used as test specimens. Each specimen was introduced into 6 ml phosphate buffer, pH 6.5, and 1500 µg of the enzyme was added. The specimen was reacted with the enzyme at 37° C. under shaking at 120 rpm. A part of the reaction solution was collected with time and filtered through 0.45 µm membrane filter, and the content of carbon (water-soluble carbon) of water-soluble organic compound in the resulting filtrate was measured to determine the rate of elution of water-soluble carbon per ml of the reaction solution per hour (µg-C/ml/h).

Figure 1:
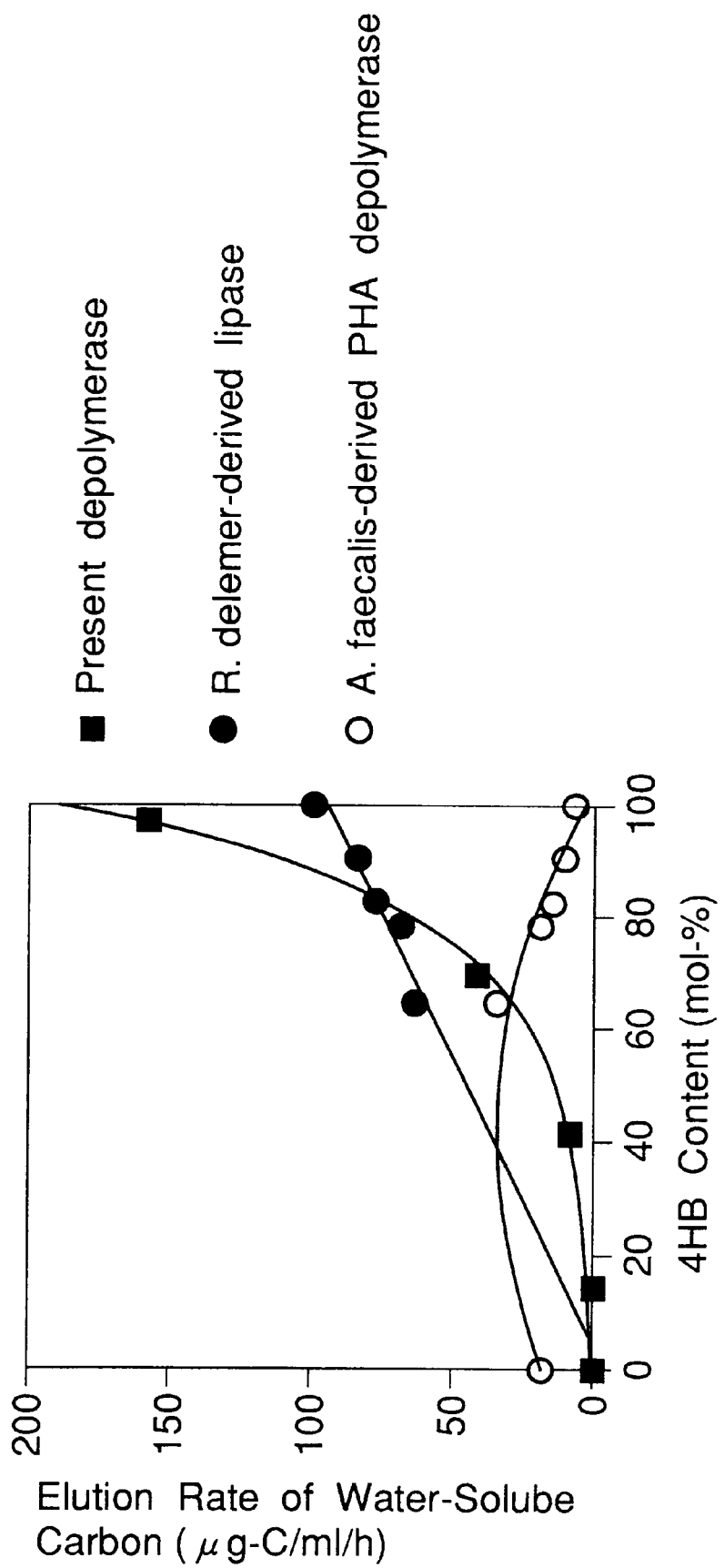
FIG. 1 shows the relationship between the content of 4HB in 3HB–4HB random copolymer and the rate of elution of water-soluble carbon by the enzyme of the present invention.

FIG. 1 shows the relationship between the content of 4HB in 3HB–4HB random copolymer and the rate of elution of water-soluble carbon. The decomposition activities of *Alcaligenes faecalis*-derived PHA depolymerase and *Rizopus delemer*-derived lipase as known decomposing enzymes are also shown. As a result, the PHA depolymerase of the present invention was characterized in that whereas it did not exhibit decomposition activity when the content of 4HB in the copolymer was 0 mol-%, its decomposition activity increased exponentially with an increasing content of 4HB. The decomposition product from a copolymer film of the copolymer with 97 mol-% 4HB was analyzed by HPLC and identified by FAB-Mass and LC-Mass, indicating that the major decomposition product was a 4HB–4HB dimer (molecular weight of 191).

(2) The activity of the present enzyme was examined on C3 to C6 straight-chain ω-hydroxyalkanoate polymers. The polymers used are shown in Table 2.

TABLE 2

|  | number average molecular weight |
| --- | --- |
| polypropyllactone (PPL) | 25,000 |
| poly-4-hydroxybutyrate (4HB) | 99,000 |
| polyvalerolactone (PVL) | 13,000 |
| polycaprolactone (PCL) | 59,000 |

Each polymer was formed into a film by solvent casting and the film was used as a test specimen. Each specimen was examined in the following manner. Each test specimen, 9 mg, was introduced into 6 ml phosphate buffer, pH 6.5. Then, 1500 μg of the enzyme was added. The specimen was reacted with the enzyme at 37° C. under shaking at 120 rpm. A part of the reaction solution was collected with time and filtered through 0.45 μm membrane filter, and the content of water-soluble carbon in the resulting filtrate was measured to determine the rate of elution of water-soluble carbon per ml of the reaction solution per hour (μg-C/ml/h).

Figure 2:
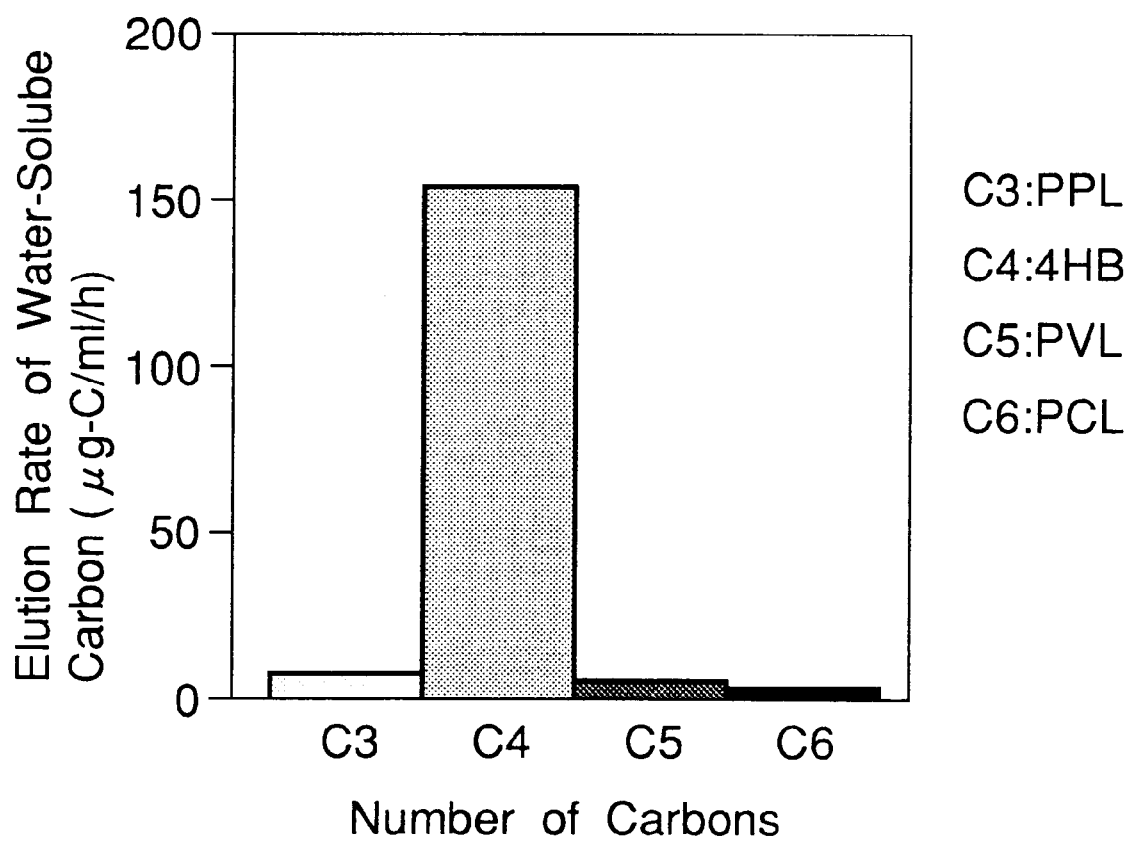
FIG. 2 shows the rate of elution, by the enzyme of the present invention, of water-soluble carbon from various ω-hydroxyalkanoate polymers.

FIG. 2 shows the rate of elution of water-soluble carbon from each polymer. From this result, it is understood that the enzyme of the present invention exerts high decomposition activity on P(4HB) among the ω-hydroxyalkanoate polymers.

2. N-terminal sequence

The N-terminal fragment 22 amino acid residues of the purified PHA depolymerase were analyzed by a protein sequencer (Model 492, Perkin Elmer). The result indicated that the N-terminal fragment had the amino acid sequence of SEQ ID NO: 1. When this sequence was examined for its homology with the N-terminal sequences of a wide variety of known enzymes, none of the enzymes agreed therewith, so it was found that the enzyme of the present invention is a novel enzyme.

3. Molecular weight

The molecular weight was about 33,000 as determined by SDS polyacrylamide gel electrophoresis.

4. Optimum pH

Figure 3:
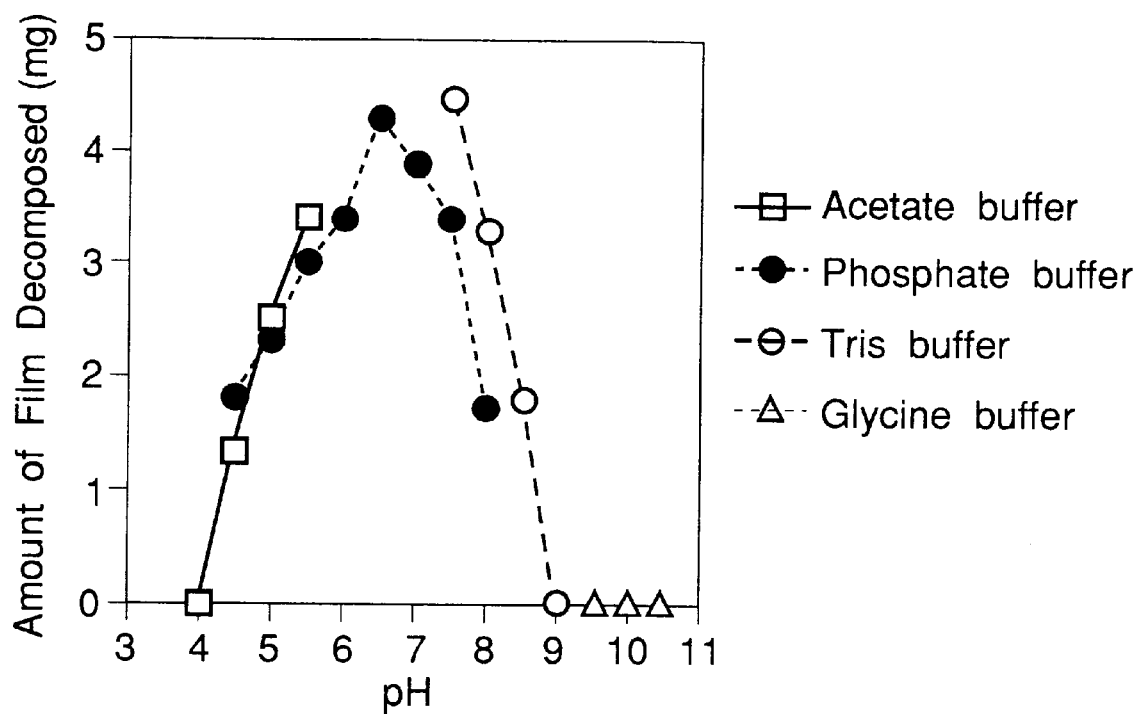
FIG. 3 shows the optimum pH of the enzyme of the present invention.

The optimum pH of the PHA depolymerase of the present invention was determined in acetate buffer (pH 4.0 to 5.5), phosphate buffer (pH 4.5 to 8.9), Tris buffer (pH 7.5 to 9.5) and glycine buffer (pH 9.0 to 10.5). The film of 3HB–4HB copolymer with 97 mol-% 4HB was used as the substrate. A 3HB–4HB copolymer film prepared by solvent casting was cut into pieces 1 by 1 cm square (about 6 mg), and each piece was placed in each buffer, and the enzyme was added at a concentration of 250 μg/ml and reacted at 30° C. for 7 hours with gentle shaking. After the reaction was finished, each film was removed and dried and its dry weight was measured to determine the amount of the decomposed film. FIG. 3 shows the relationship between the pH and the amount of the decomposed film. As shown in FIG. 3, the decomposition was confirmed in the range of pH 4 to 9, and the highest decomposition was observed at pH 6.5. This result indicated that the optimum pH is in the range of 5 to 8.

5. Optimum temperature

Figure 4:
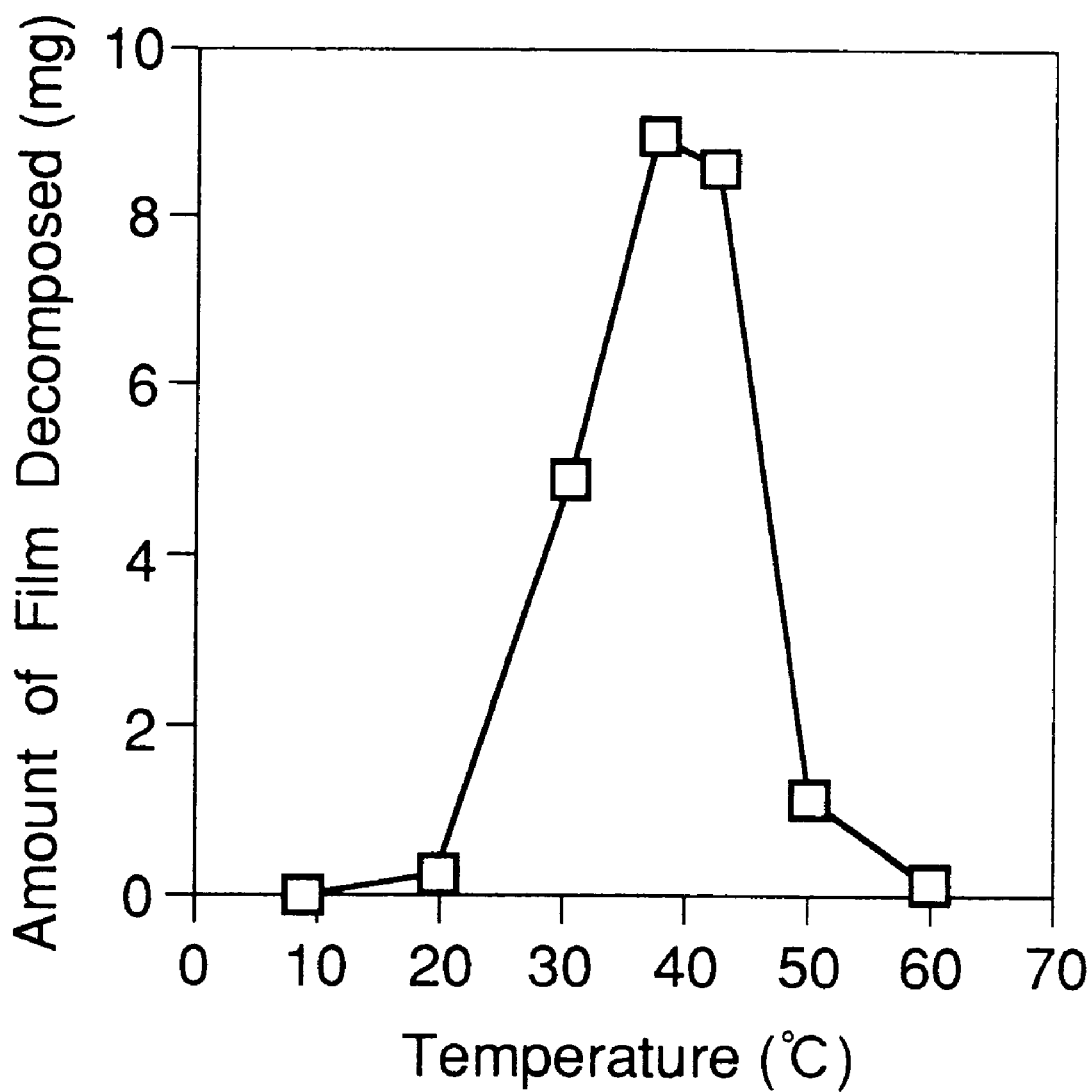
FIG. 4 shows the optimum temperature of the enzyme of the present invention.

250 μg of the enzyme was added to 1 ml phosphate buffer, pH 6.5, and one piece (1 by 1 cm square, about 6 mg) cut from a film of 3HB–4HB copolymer with 97 mol-% 4HB was introduced into the buffer and reacted at various temperatures for 7 hours with gentle shaking. After the reaction was finished, each film was removed and dried and its dry weight was measured to determine the amount of the decomposed film. FIG. 4 shows the relationship between the temperature and the amount of the decomposed film. As shown in FIG. 4, the decomposition was confirmed in the range of 20 to 60° C., and the optimum temperature was in the range of 37 to 42° C.

6. Temperature stability

Figure 5:
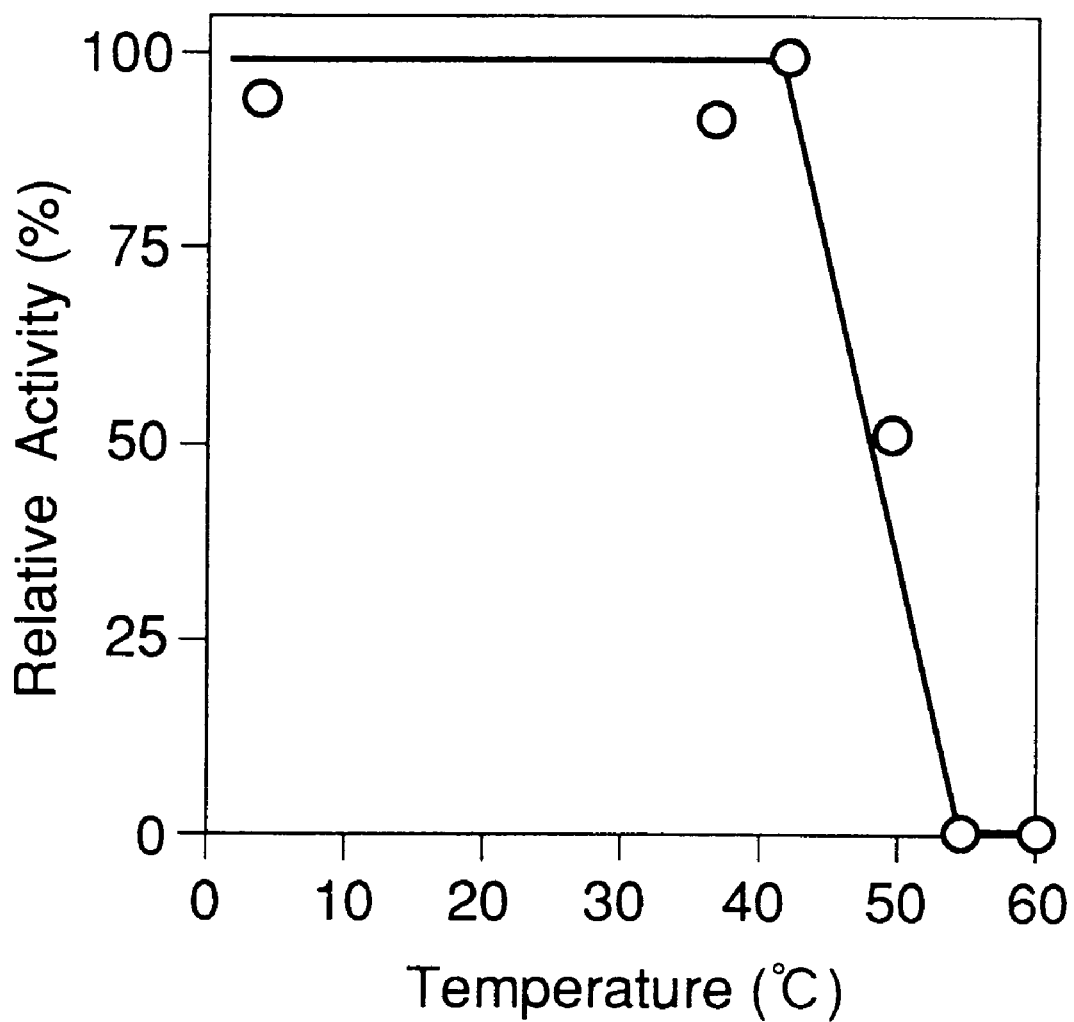
FIG. 5 shows the temperature stability of the enzyme of the present invention.

1500 μg of the enzyme was added to 6 ml phosphate buffer, pH 6.5 and shaken gently at various temperatures for 30 minutes. Thereafter, one piece (1 by 1 cm square, about 6 mg) cut from a film of 3HB–4HB copolymer with 97 mol-% 4HB was introduced into the buffer. The solution was incubated at 37° C. under shaking. A part of the reaction solution was collected with time and filtered through 0.45 μm membrane filter, and the content of water-soluble carbon in the resulting filtrate was measured to determine the rate of elution of water-soluble carbon per ml of the reaction solution per hour (μg-C/ml/h). FIG. 5 shows the relative activity after treatment at various temperatures when the activity before treatment is 100% in terms of elution rate. As shown in FIG. 5, the activity drastically dropped at elevated temperatures of more than 42° C. Accordingly, the present enzyme is stable at a temperature of up to 42° C.

7. Isoelectric point

The isoelectric point as determined by acrylamide gel electrofocusing was about 8.6.

8. Effects of various substances

Phenylmethylsulfonyl fluoride (PMSF), dithiothreitol (DTT) or diisopropyl fluorophosphate (DFP) was added as an inhibitor at predetermined concentrations to 6 ml phosphate buffer (pH 6.5) containing 1500 μg of the enzyme. Further, one piece (1 by 1 cm square, about 6 mg) cut from a film of the copolymer with 97 mol-% 4HB was introduced into each enzyme solution containing each inhibitor at a predetermined concentration. The solution was incubated at 37° C. under gentle shaking. A part of the reaction solution was collected with time and filtered through 0.45 μm membrane filter, and the content of water-soluble carbon in the resulting filtrate was measured to determine the amount of water-soluble carbon in it. The relative activity at various concentration of the inhibitor was determined when the activity in the absence of the inhibitor was 100% in terms of elution rate of water-soluble carbon per ml of the reaction solution per hour. Table 3 shows the concentration of each inhibitor at which the enzyme activity was inhibited by 50% ($IC_{50}$). The $IC_{50}$ of DFP was 0.15 μM, demonstrating particularly significant inhibitory effect.

TABLE 3

| Inhibitor | $IC_{50}$ |
| --- | --- |
| PMSF | 1.92 mM |
| DTT | 73 mM |
| DFP | 0.15 μM |

The microorganism used in production of the PHA depolymerase of the present invention may be any strain belonging to the genus Corynebacterium and having the ability to produce the PHA depolymerase. Such microorganisms include e.g. *Corynebacterium acruaticum* IM-1 etc.

This IM-1 strain, similar to other microorganisms, is liable to changes in its properties and can be mutated by artificial means such as UV light, X-ray, chemicals etc. and such mutants or variants can also be used insofar as they have the activity similar to that of IM-1 strain.

The microbiological properties of the IMI-1 strain are as follows:

1. Morphological properties

Trophic cells of IM-1 strain grown in CGY medium (5 g/l casiton, 5 g/l glycerol, 1 g/l yeast extract) were bacillus with 0.5 to 0.7×1.5 to 3.0 microns in size. This microorganism did not form spores in incubation at 30° C. for 2 days, and it was Gram-positive bacillus with polymorphism rendering cells globular.

2. Cultural properties

The IM-1 strain grows in a usual bacterial medium in incubation at 25 to 40° C. for 1 to 3 days.

3. Physiological properties (1) Attitude toward oxygen: aerobic
(2) Acid-fast: negative
(3) Acid resistance: negative
(4) Rod-coccus cycle: positive
(5) Colony color: yellowish
(6) Reduction of nitrate: negative
(7) Oxidase: negative
(8) Galactase: positive
(9) β-glucuronidase: negative
(10) β-glucosidase: positive
(11) N-acetyl-β-glucosidase: positive
(12) Urease: negative
(13) Hydrolysis of starch: positive
(14) Fermentation with glucose: negative
(15) Utilization of sugars: no growth in ribose, xylose, mannitol, maltose, lactose, sucrose, or glycogen.

The IM-1 strain showing the above bacterial properties was identified using API Coryne series and compared with known bacterial species described in Bergey's Manual of Determinative Bacteriology, and as a result the IM-1 strain was identified as *Corynebacterium aguaticum*. *Corynebacterium aquaticum* IM-1 was deposited as FERM BP-6160 on Nov. 13, 1996 with the National Institute of Bioscience and Human-Technology, Agency of Industrial Science and Technology, Japan.

To produce the PHA depolymerase by use of microorganisms of the genus Corynebacterium, their cells are multiplied by culturing aerobically in a CGY medium or a natural medium such as nutrient broth or the like, then recovered and transferred to a medium for inducing PHA depolymerase, followed by further aerobic culture.

The medium used for inducing the PHA depolymerase includes a medium containing acetic acid, propionic acid, butyric acid, fumaric acid, butanol, methanol, triolein, paraffin, 4-hydroxybutyric acid or poly-4-hydroxybutyric acid as a sole carbon source and ammonium chloride or ammonium sulfate as a sole nitrogen source, and further magnesium sulfate.

Culture is carried out aerobically e.g. under aeration with stirring. The culture temperature is usually 25 to 37° C., preferably 27 to 32° C. The initial pH of the induction medium is usually 6.0 to 8.0, preferably 7.0 or thereabout. The period of culture is usually 20 to 96 hours, preferably 40 to 96 hours.

Separation and purification of the PHA depolymerase from the culture can be effected by subjecting the culture to centrifugation to remove the microorganism and purifying the resulting supernatant using conventional enzyme purification means such as column chromatography, fraction-ation precipitation with ammonium sulfate, gel filtration etc. The purified PHA depolymerase can thus be obtained.

Further the PHA depolymerase of the present invention can also be produced by culturing in a medium a transformant transformed with a recombinant vector containing a gene of the enzyme and then recovering the enzyme from the resulting culture. The gene of the PHA depolymerase of the present invention can be separated from e.g. *Corynebacterium aquaticum* IM-1, and a transformant transformed with a recombinant vector containing the gene can be obtained in the following manner. Based on the N-terminal amino acid sequence (i.e. the amino acid sequence of SEQ ID NO:1) of the PHA depolymerase, a DNA probe containing a nucleotide sequence coding for the whole or a part of the amino acid sequence is chemically synthesized. Separately, *Corynebacterium aquaticum* IM-1 is cultured aerobically in a CGY medium or in a natural medium such as nutrient broth or the like and then collected, followed by extraction and purification of its genomic DNA in a usual manner. The purified genomic DNA is cleaved with a suitable restriction enzyme to give a DNA fragment mixture. By Southern hybridization using the above synthetic DNA probe, a DNA fragment hybridizing with the DNA probe is obtained from the DNA fragment mixture. The DNA fragment thus obtained is inserted in or ligated to a cloning vector previously cohesive-ended by treatment with a restriction enzyme. The cloning vector may be any plasmid vector or phage vector used in usual cloning. The recombinant vector thus obtained is used to transform a host, and a desired transformant can be obtained by colony hybridization. The host used may be *E. coli* etc.

According to the present invention, there can be provided novel PHA depolymerase having the activity of decomposing ω-hydroxyalkanoates, particularly 4HB homopolyester or copolymerized polyesters containing said homopolyester, as well as a process of efficiently producing the enzyme.

EXAMPLES

Hereinafter, the present invention is described in more detail with reference to the Examples, which however are not intended to limit the scope of the present invention.

Example 1

Three 3-L jar fermenters were charged respectively with 2 L of an induction medium containing 5 g/l sodium 4-hydroxybutyrate, 1 g/l $NH_4Cl$, and 0.5 g/l $MgSO_4.7H_2O$ and then the medium was sterilized at 121° C. for 15 minutes. *Corynebacterium aguaticum* IM-1, pre-cultured in 500 ml Erlenmeyer flask containing 100 ml CGY liquid medium, was inoculated aseptically into each fermenter and cultured at 30° C. for 24 hours under aeration with stirring. During culture, the pH was maintained at 7.0 with $1N—H_2SO_4$.

After culture was finished, the culture was centrifuged at 6000 rpm for 30 minutes to give a culture supernatant. Then, it was passed through an ultrafiltration membrane with a cut-off molecular weight of 30,000 (Dicel: FB02-CC-FUY03AI) whereby a fraction with a molecular weight of 30,000 or more was recovered. The fraction with a molecular weight of 30,000 or more was concentrated in an evaporator to give 35 ml crude enzyme solution. The crude enzyme solution was applied to a column of 450 ml Sephadex G-50 (length, 900 mm; diameter, 30 mm) and developed with distilled water. The eluate, 10 ml per fraction, was recovered and 0.1 ml of each fraction was dropped into a PHA agar plate in which powder of 3HB–4HB copolymer with 97 mol-% 4HB was suspended, and the enzyme activity was determined in terms of the diameter of the resulting clear zone around the spot.

Figure 6:
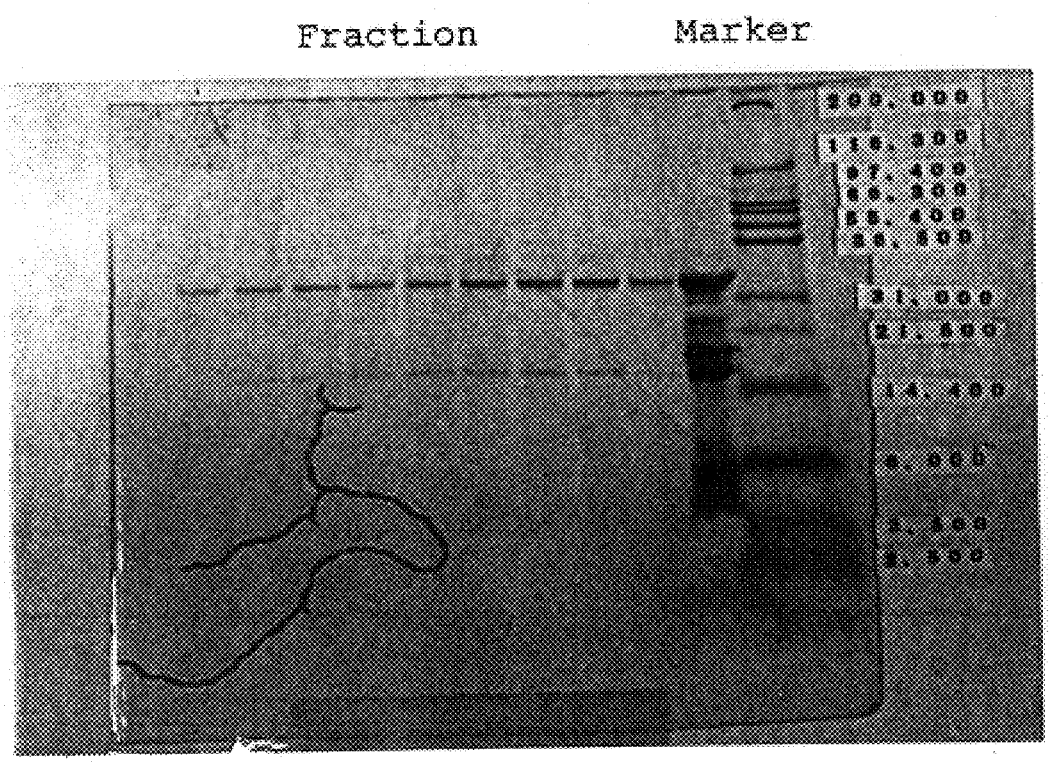
FIG. 6 shows a profile in SDS-PAGE of the enzyme of the present invention.

The fractions whose PHA decomposition activity was confirmed were collected and concentrated, and then lyophilized to give 360 mg crude enzyme powder. Then, 360 mg crude enzyme powder was dissolved in 15 ml distilled water and applied to a column of 450 ml Toyo Pearl HW50 (Fine) (length 900 mm, diameter 30 mm) and developed with distilled water. Fractions with PHA decomposition activity were collected and finally 230 mg enzyme was obtained. When the respective fractions were subjected to SDS-PAGE, all of them indicated a single band. FIG. 6 shows a profile in SDS-PAGE. In FIG. 6, the rightmost band is derived from a molecular weight marker, the second band from the right is derived from the fraction with confirmed PHA decomposition activity after application to Sephadex G-50, and the third and subsequent bands from the right are derived from the fractions with confirmed PHA decomposition activity after application to Toyo Pearl HW 50.

What is claimed is:

1. A purified polypeptide having a N-terminal fragment of the amino acid sequence of SEQ ID NO: 1; having a molecular weight of about 33,000 as determined by SDS polyacrylamide gel electrophoresis; and having polyhydroxyalkanoate depolymerase activity.

2. A process for producing polyhydroxyalkanoate depolymerase, comprising culturing in a medium a microorganism which belongs to the genus Corynebacterium and has the ability to produce the polypeptide of claim 1 and recovering the polypeptide from the resulting culture.

3. A process for producing polyhydroxyalkanoate depolymerase, comprising culturing in a medium a transformant transformed with a recombinant vector containing a gene of the polypeptide of claim 1 and recovering the polypeptide from the resulting culture.

* * * * *

SEQUENCE LISTING

<160> NUMBER OF SEQ ID NOS: 1

<210> SEQ ID NO 1
<211> LENGTH: 22
<212> TYPE: PRT
<213> ORGANISM: Corynebacterium sp.

<400> SEQUENCE: 1

```
Ala Gly Pro Val Thr Leu Glu Ala Thr Phe Thr Ser Ser Cys Cys Gly
 1               5                  10                  15

Trp Glu Lys Val Glu Arg
            20
```